(12) United States Patent
Xu et al.

(10) Patent No.: US 8,338,372 B2
(45) Date of Patent: Dec. 25, 2012

(54) DEHYDROXY VANCOMYCIN, THE PREPARATION, PHARMACEUTICAL COMPOSITION AND THE USE

(75) Inventors: Bingxiang Xu, Huancheng Donglu (CN); Haisong Xie, Huancheng Donglu (CN); Huan Yu, Huancheng Donglu (CN); Wei Mao, Huancheng Donglu (CN); Weidong Ye, Huancheng Donglu (CN)

(73) Assignees: Zhejiang Medicine Co., Ltd., Zhejiang Province (CN); Xinchang Pharmaceutical Factory

( * ) Notice: Subject to any disclaimer, the term of this patent is extended or adjusted under 35 U.S.C. 154(b) by 401 days.

(21) Appl. No.: 12/680,650

(22) PCT Filed: Aug. 25, 2008

(86) PCT No.: PCT/CN2008/001524
§ 371 (c)(1),
(2), (4) Date: May 12, 2010

(87) PCT Pub. No.: WO2009/046618
PCT Pub. Date: Apr. 16, 2009

(65) Prior Publication Data
US 2010/0222252 A1   Sep. 2, 2010

(30) Foreign Application Priority Data

Sep. 20, 2007   (CN) .......................... 2007 1 0152027

(51) Int. Cl.
*A61K 38/14* (2006.01)
*C07K 9/00* (2006.01)
*C07K 1/22* (2006.01)
*A61P 31/04* (2006.01)

(52) U.S. Cl. .............................. 514/8; 530/322; 530/344
(58) Field of Classification Search .................... None
See application file for complete search history.

(56) References Cited

U.S. PATENT DOCUMENTS

| 2,918,477 | A | 12/1959 | Cattapan et al. |
| 2010/0144828 | A1 | 6/2010 | Wu et al. |
| 2010/0311827 | A1 | 12/2010 | Daneshtalab et al. |

FOREIGN PATENT DOCUMENTS

| CN | 1175411 | 3/1998 |
| CN | 1415758 | 5/2003 |
| CN | 1657601 | 8/2005 |
| EP | 0159180 | 10/1985 |
| EP | 0265071 | 4/1988 |
| EP | 1200462 | 5/2005 |
| JP | 2006 298802 | 11/2006 |
| WO | 9809964 | 3/1998 |
| WO | 2004052310 | 6/2004 |
| WO | 2005118585 | 12/2005 |
| WO | 2007030657 | 3/2007 |
| WO | 2008098471 | 8/2008 |
| WO | 2009046618 | 4/2009 |

OTHER PUBLICATIONS

CDC, "Human Immunodeficiency Virus Type 2," Oct. 1998.
Kashman, et al., "The Calanolides, a Novel HIV-Inhibitory Class of Coumarin Derivatives from the Tropical Rainforest Tree, *Calophyllum lanigerum*," J. Med. Chem. 1992;35, pp. 2735-2743.
Dittmar, et al., "HIV: Epidemiology and Strategies for Therapy and Vaccination," PubMed, Intervirology, 2002;45(4-6), pp. 260-266.
Miles, K. "The Growing HIV Pandemic," PubMed, Community Pract. Aug. 2005;78(8), pp. 292-294.
The Merck Manual, "Human Immunodeficiency Virus (HIV)," pp. 1-16, Accessed Aug. 27, 2009.
The Merck Manual, "Respiratory Viruses," pp. 1-2, Accessed Aug. 27, 2009.
Morissette, et al., "High-Throughput Crystallization: Polymorphs, Salts, co-Crystals and Solvates of Pharmaceutical Solids," Advanced Drug Delivery Reviews 2004, 56, pp. 275-300.
Souillac, et al., "Characterization of Delivery Systems, Differential Scanning Calorimetry," Encyclopedia of Controlled Drug Delivery, 1999, pp. 212-227, John Wiley & Sons.
Vippagunta, et al., "Crystalline Solids," Advanced Drug Delivery Reviews, 2001, 48, pp. 3-26.
Ma, et al., "Synthesis of Chlorogenic Acid Derivatives with Promising Antifungal Activity," Bioorganic & Medicinal Chemistry, 2007, 15, pp. 6830-6833.
The Merck Manual, "Acute Viral Hepatitis," pp. 1-8, Accessed Aug. 27, 2009.

*Primary Examiner* — Scott Long
*Assistant Examiner* — Sarah Alawadi
(74) *Attorney, Agent, or Firm* — Daniel A. Thomson; Emerson Thomson Bennett LLC

(57) ABSTRACT

The present invention provides a deshydroxy vancomycin compound, a method of its preparation and a pharmaceutical composition comprising a pharmaceutically effective amount of the deshydroxy vancomycin and the use of the said composition in the preparation of drugs for the treatment of susceptible bacteria infections. The method includes the following steps: (1) preparing a concentrated vancomycin solution containing the deshydroxy vancomycin by fermentations of *Amycolatopsis Orientalis* with Deposit No. CGMC-CNO.1183; (2) separating and purifing the concentrated vancomycin solution to obtain a refined filtrate of vancomycin hydrochloride containing the deshydroxy vancomycin by column chromatography; and (3) further separating and purifing the refined filtrate to obtain the deshydroxy vancomycin by chromatography. Wherein, separation and purification is processed by column chromatography in a gel chromatography column containing a salt-water mobile phase, separation and purification is processed by chromatography in a macroporous adsorption resin chromatography column containing a buffer-methanol mobile phase.

13 Claims, 1 Drawing Sheet

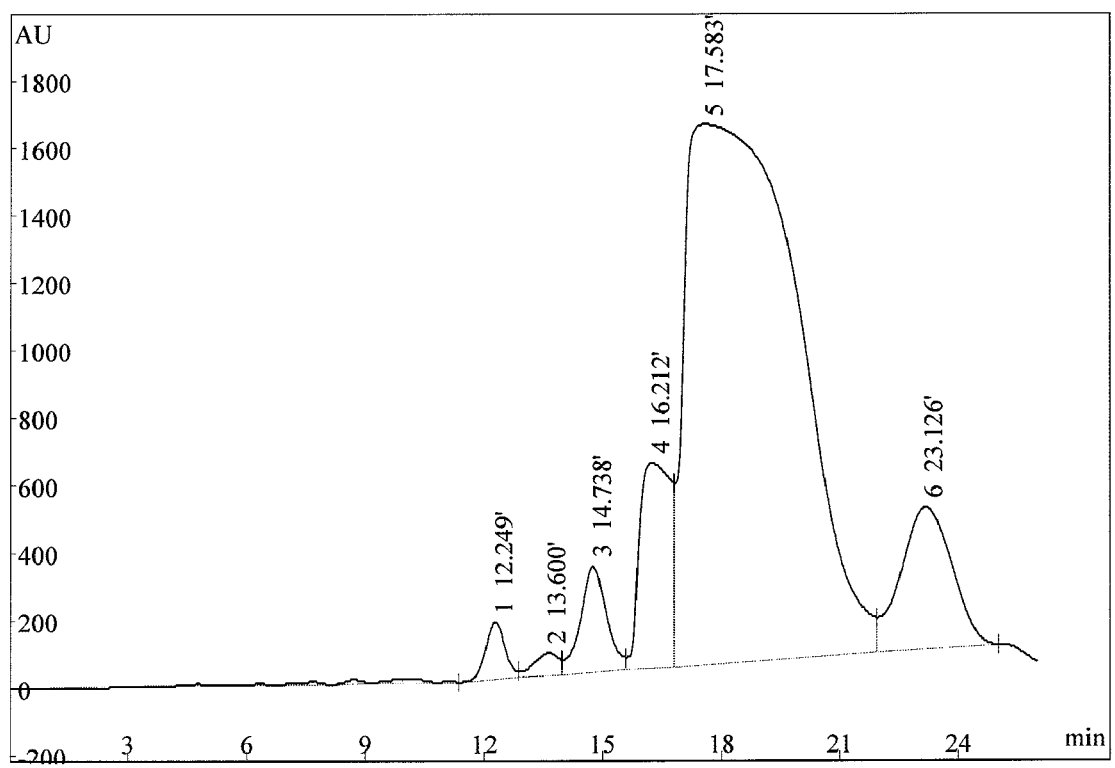

DEHYDROXY VANCOMYCIN, THE PREPARATION, PHARMACEUTICAL COMPOSITION AND THE USE

FIELD OF THE INVENTION

The present invention relates to novel vancomycin derivatives. In particular, the vancomycin derivatives are prepared by fermentations of *Amycolatopsis orientalis* (Deposit No.: CGMCC NO.1183), and are separated and purified by the chromatogram. The deposit of *Amycolatopsis* was received and registered on Jul. 1, 2004 at Institute of Microbiology, Chinese Academy of Sciences, No. 13, Zhongguancun, Haidan district, Beijing 100080 China, under the Budapest Treaty. Access to the deposit will be available during pendency of the patent application, and all restrictions imposed by the depositor on the availability to the public of the deposited material will be irrevocably removed upon the granting of the patent.

BACKGROUND OF THE INVENTION

The vancomycin is a glycopeptide antibiotics having bactericidal actions developed in 1950s, especially having strong bactericidal actions on gram-positive cocci. Recently, infections of methicillin-resistant *Staphylococcus aureus* are present due to increases of infections of *Staphylococcus epidermidis*, it makes actions of vancomycin more important in clinic. Therefore, vancomycin is a preferred drug in treatments of serious infections caused by methicillin-resistant *Staphylococcus Aureus* in clinic at present. Because of the specfic mechanism of vancomycin and features of easy decomposition in vivo of polypeptide antibiotics of vancomycin, it has been widely applied in clinic.

Besides, there have been congeneric drugs of demethyl vancomycin in China. The experimental results show that the demethyl vancomycin can effevtively inhibit colonization and reproduction of *Clostridium difficile* in intestine and consequently eliminate its pathogenicity as vancomycin. The demethyl vancomycin is a specific drug for treatment of *Clostridium difficile*-associated pseudomembranous enterocolitis with strong antibacterial actions and is also an effective drug for treatment of infections of anaerobic bacterium and some gram-positive bacterium. The demethyl vancomycin with good pharmacokinetical properties can not produce drug resistance easily, and can not produce cross-resistance with other antibiotics. But, the demethyl vancomycin can not replace of imported vancomycin all the time.

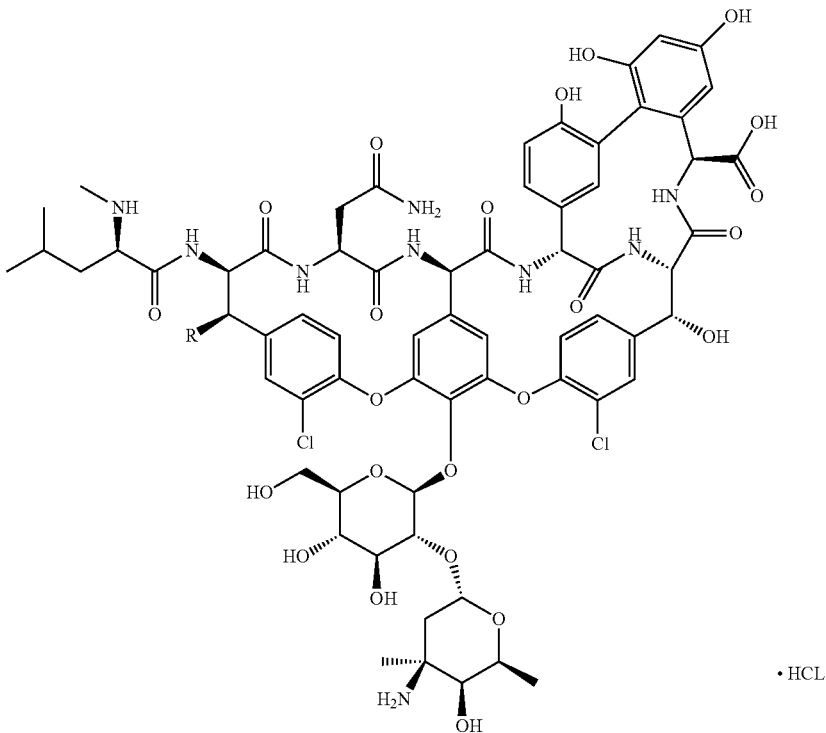

In recent years, it is an urgent need to develop novel antibiotics for treatment of human diseases. The known antibiotic substances are usually modified on the molecular structure to develop new drugs. But, such structural modification usually result in new substances loss activity required. There are multiple derivatives produced in the fermentation product of vancomycin, and different fermentation strains also result in differences of derivatives. We find from reported references that various derivatives of vancomycin are listed in the patent (Patent No. EP0159180) filed by American Lilly Company, such as M43A, M43B, M43C, M43D respectively, and their structures are as follows:

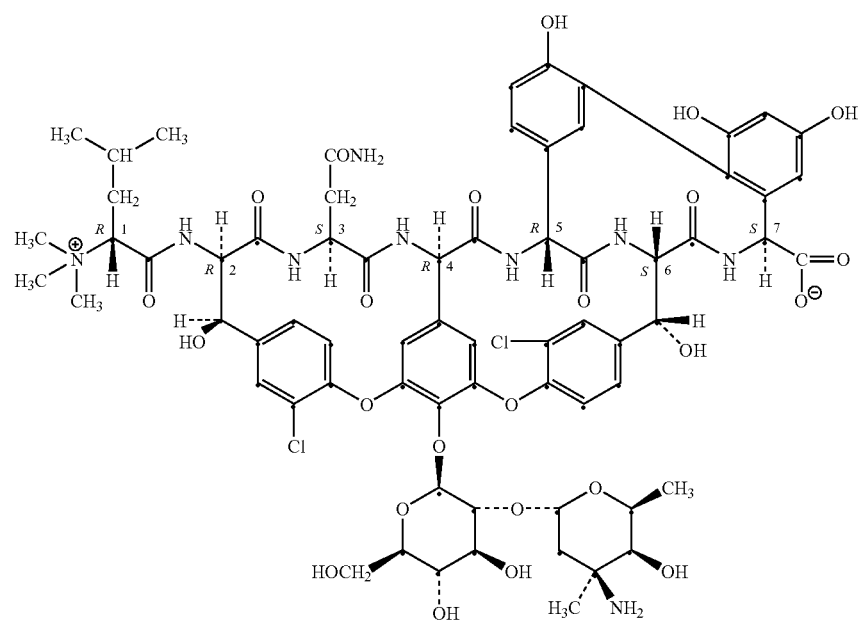
M43A
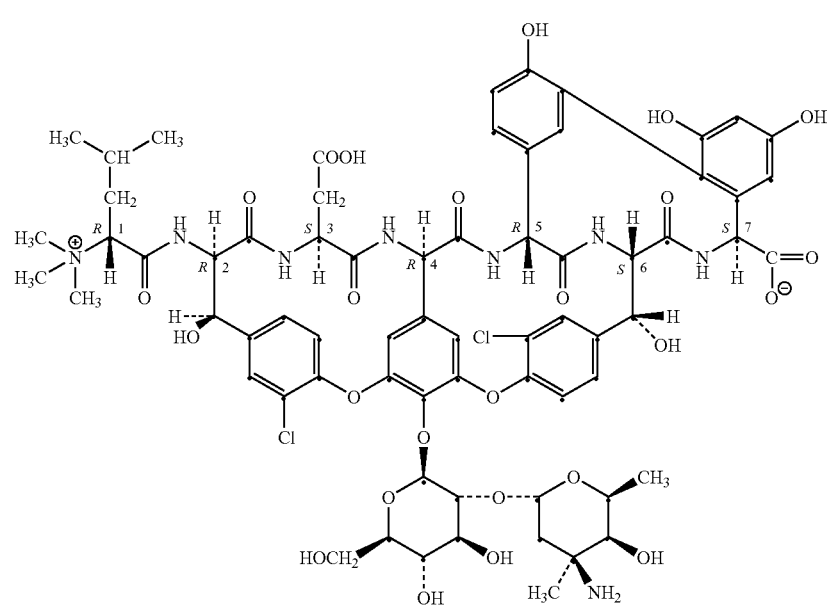
M43B

-continued

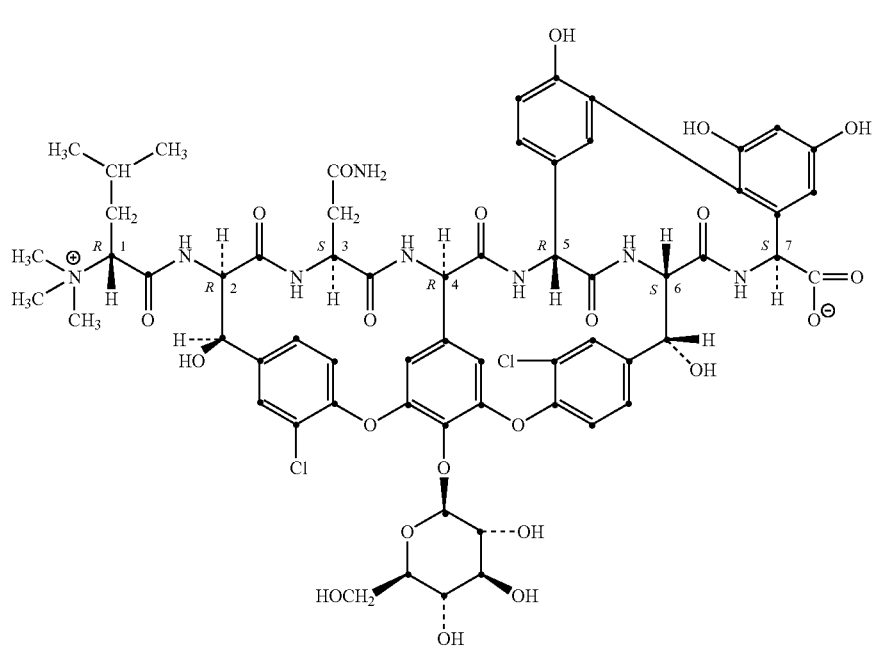

M43C

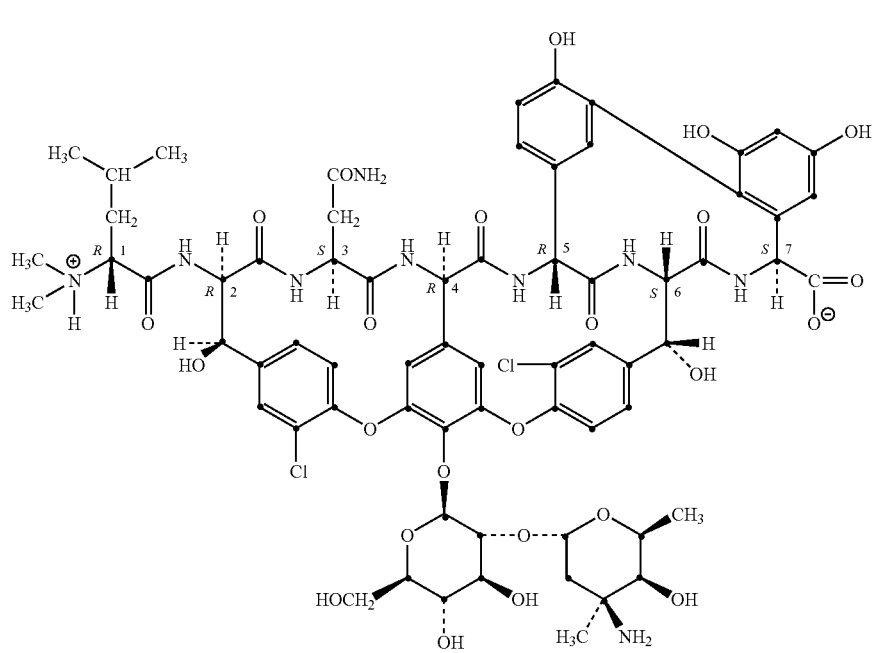

M43D

The inventor of the present application finds a novel derivative of vancomycin, dehydroxy vancomycin from fermentation products of vancomycin hydrochloride. We confirm that this dehydroxy vancomycin is a novel substance to be different from the above-mentioned four kinds of derivatives of vancomycin through their molecular structures. In particular, the structure of dehydroxy vancomycin is extremely similar to that of vancomycin. In light of good antibacterial activities of vancomycin, it can be foreseen that it will be very likely to become a novel antibiotics if the dehydroxy vancomycin is known clearly.

SUMMARY OF THE INVENTION

The purpose of the present invention is to obtain a novel vancomycin derivative produced by fermentations of vancomycin. In particular, the present invention provides a dehydroxy vancomycin having the General Formula I as follows.

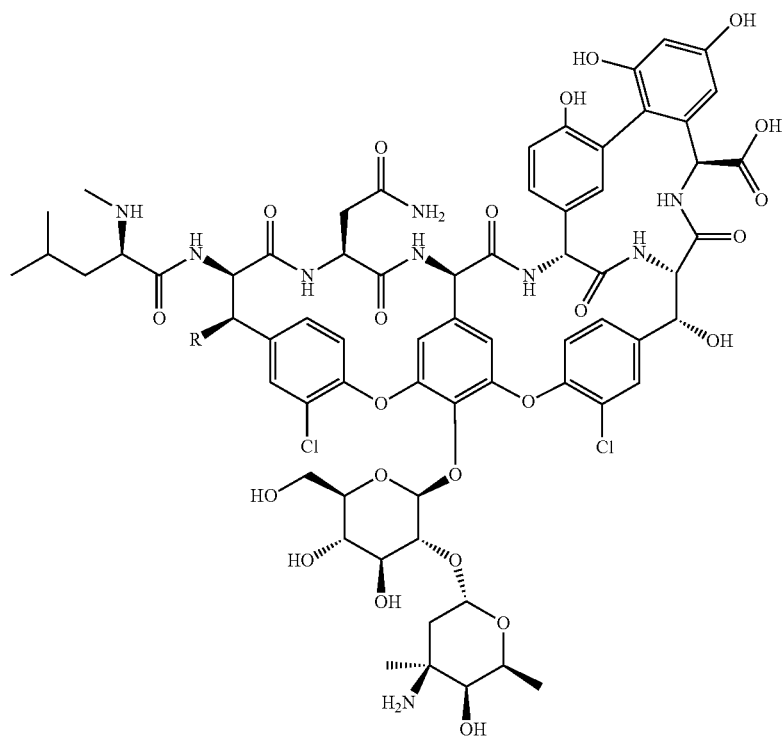

Wherein, R of the dehydroxy vancomycin in the General Formula I is H. So the difference between vancomycin and dehydroxy vancomycin is that R of the dehydroxy vancomycin molecule is H and R of the vancomycin molecule is OH.

The present invention also provides a method for preparing the dehydroxy vancomycin, comprising the following steps:

(1) preparing a concentrated vancomycin solution containing the dehydroxy vancomycin by fermentations of *Amycolatopsis Orientalis* with Deposit No. CGMCCNO.1183:

(2) separating and purifying the concentrated vancomycin solution to obtain a refined filtrate of vancomycin hydrochloride containing the dehydroxy vancomycin by column chromatography; and (3) further separating and purifying the refined filtrate to obtain the dehydroxy vancomycin by chromatography.

Wherein, in the step (2), separation and purification is processed by column chromatography in a gel chromatography column containing a salt-water mobile phase;

In the step (3), separation and purification is processed by chromatography in a macroporous adsorption resin chromatography column containing a buffer-methanol mobile phase.

Wherein, pH of said concentrated vancomycin solution is adjusted to 2.8. In the gel chromatography column, said mobile phase is 0.1M aqueous solution of $NH_4HCO_3$. Said gel is dextran gel, polyacrylamide gel, agarose gel and polystyrene gel.

It comprises nanofiltrating, concentrating and desalting the column chromatography solution by using 0.22 μm microporous filter membrane in the separation and purification of column chromatography.

In addition, said mobile phase includes buffer:methanol=92:8 in the separation and purification of chromatography. Said buffer comprises triethylamine and phosphoric acid, and pH=3.2. Said macroporous adsorption resin is Rohm & Hass macroporous adsorption resin.

In view of dehydroxy vancomycin is a byproduct of vancomycin, the processes of them are consistent before separation and purification of chromatography, i.e. dehydroxy vancomycin and vancomycin are prepared by fermentations of *Amycolatopsis Orientalis*. So vancomycin is prepared by fermentations of *Amycolatopsis Orientalis* (CGMCC NO.1183) before separation and purification of chromatography. This method refers to the Chinese Patent Application No. 200410067197.7 filed by the present applicant on Oct. 15, 2004. According to the present invention, the method of preparing for dehydroxy vancomycin are as follows:

1. Preparing vancomycin containing dehydroxy vancomycin by fermentations of *Amycolatopsis Orientalis*

(1) Choosing and Determining Formula of the Medium

The formula of slant medium, seed medium and fermentation medium having high and stable fermentation level are determined by studying types and concentrations of carbon source, nitrogen source and inorganic salt.

(2) Slant Medium

Gao No.1 slant medium is used as the slant medium of vancomycin producing stains, through choosing and comparing different formula of medium. The details of formula are as follows:

Soluble starch 2.0%;
NaCl 0.05%;
$KNO_3$ 0.1%;
$MgSO_4$ 0.05%;
$FeSO_4$ 0.001%;
$KH_2PO_4$ 0.05%;
Agar 2.2%
pH 7.2-7.4 after sterilizing The slant medium is cultured at 28° C. for 7 days after inoculation. The well growth slant is chubbiness with off-white on its surface. The colony looks like a bread-type with light grey ring patterns on its surface. The spore looks like a milk white with 3-5 mm of its diameter.

(3) Seed Medium

The seed medium of vancomycin producing stains is determined through choosing and comparing different medium formula. The details of formula are as follows:
Soluble starch 4.0%;
Glucose 1.5%;
Glycerol 2.0%;
Soybean cake powder (hot-press) 2.0%;
$KNO_3$ 0.6%;
$KH_2PO_4$ 0.02%;
$MgCl_2$ 0.02%;
Defoamer GPE 0.06%
pH 6.8 before sterilizing Volume of seed medium in flask is about 100 ml volume of seed medium in flask with 750 ml volume; Culture temperature is about 28□; Culture time is about 48 hours; pH of seed solution with well growth is about 7.7 and its appearance shows a milk-yellow; the amount of mycelium is about 22% after centrifugalization for 10 min at 4000 rpm. When mycelial is strong and no mixed mycelial in the seed solution, the seed solution can be inoculated into next seed tank or lab fermentor.

(4) Fermentation Medium

The seed medium of vancomycin producing stains is determined by choosing and comparing different medium formulas. The concrete formula are as follows:
glycerol 6.0%;
soybean cake meal (hot-press) 2.0;
$KH_2PO_4$ 0.02%;
$MgCl_2$ 0.02%;
$KNO_3$ 0.6%;
$CaCl_2$ 0.3%;
pH before sterilizing 6.8

(5) Choosing and Determining Conditions of Fermentations

The conditions of fermentation of flask and 10 L glass fermentor are determined by tests. The conditions of fermentation comprise temperature of fermentation, pH, rotational speed of shaker, volume of seed medium in flask, amount of aeration of glass fermentor, rotational speed of stir and so on.

(6) Temperature of Fermentations

The fermentation tests are respectively processed at 25° C., 28° C. and 30° C. in flask. It proves from the result of the fermentation tests that the level of fermentation is the highest one at 28° C. and the byproduct in the fermentation broth is the least at 28° C. comparing other two temperatures. Therefore, the fermentation temperature of vancomycin is at 28° C.

(7) The Best pH for Fermentations

The fermentation tests are respectively processed at the initial pH 6.5, 6.8 and 7.0 of the fermentation medium in flask. It proves from results of fermentation tests that the level of fermentation is the highest at pH 6.8, the color of the fermentation broth is the most shallow at pH 6.8 and the byproduct in the fermentation broth is less at pH 6.8 comparing other two pH. Therefore, the initial pH of the fermentation medium is about 6.8.

(8) Other Conditions of Fermentation

Cycle of fermentation: The cycle of fermentation in flask is about 6 days, and the cycle of fermentation in fermentor is about 5-6 days.

Volume of seed medium in flask: The level of fermentation is the highest when 750 ml flask is filled with 100 ml seed medium.

Parameters of 10 L glass fermentor: The amount of aeration is about 1:1 (vol:vol), and the rotational speed of stir is about 550 rpm.

2. The Separation and Purification of Vancomycin Hydrochloride Containing Dehydroxy Vancomycin (1) Pretreatment of Fermentation Broth Vancomycin in the fermentation broth exists in the form of free alkali because pH of the fermentation broth is about 7.7 when the fermentation of vancomycin is over. The first step of the separation and purification is to adsorb vancomycin to macroporous adsorption resin (D1300) by exchange adsorptions. This process of exchange is required existing of antibiotic in the form of free acid. Therefore, the fermentation broth is acidified and its pH is adjusted to about 3.2 by dilute hydrochloric acid. In the process of acidification, flocculating agents and filter aids can be added in order to make fermentation broth be filtered easily and obtain fermentation filtrate with well quality.

(2) Adsorption, Desalting and Decolorization

In order to further separate vancomycin from other water-solubility impurity in the fermentation filtrate, it needs to make fermentation filtrate pass resin column filled with carboxylic macroporous adsorption resin. Antibiotic is eluted from resin column by aqueous solution of ethanol after washing other impurity by water.

The present invention uses D1300 resin as absorption resin. The pH of the fermentation filtrate is adjusted to about 4.5 by 4N NaOH before using resin column to absorb the fermentation filstrate. The elution solution is 80% acid aqueous solution of ethanol (pH=2.0). The elution solution is analysed and tested by HPLC. It can be obtained that the integral area ratio of vancomycin is usually about 75% and the average unit of vancomycin is above 10,000 μg/ml.

The elution solution obtained from the above process is concentrated and desalted by nanofiltration, then is decolorized by active carbons. Iron ion is removed by adding adequate sodium ferrocyanide and zinc sulfate. The above solution is collected and then desalted and concentrated by nanofiltration, then is decolorized by active carbons after adding 4N hydrochloric acid in order to adjust pH to about 2.8. The concentrated solution has been desalted and decolorized is obtained after using sodium ferrocyanide and zinc sulfate to remove iron ion in order to meet the requirement of column chromatography purification.

(3) Purification of Column Chromatography

Finally, it may determine the chromatography media of chromatography column is Sephadex C-25 by lots of tests of chromatography medias. The optimal solution of purification is determined after studing conditions of column chromatography, elution agent, manner of elution and so on. This solution of purification includes gradient elution by 0.1M aqueous solution of $NH_4HCO_3$, and then sectionally collect the elution solution and obtain the refined filtrate of chromatography after the eligible portion being merged and concentrated and desalted by nanofiltration.

The above concentrated solution passes Sephadex C-25 gel chromatography column and is further separated and purified according to the requirement of process. The refined filtrate of chromatography is obtained after the above purified solution of chromatography is merged and concentrated and desalted by nanofiltration. The eligible refined filtrate is decolorized by active carbons and is filtered to remove hot source by 0.22 μm microporous filter membrane. The refined filtrate of vancomycin hydrochloride is lyophilized to obtain lyophilized powder of vancomycin hydrochloride containing dehydroxy vancomycin hydrochloride.

3. Preparing High Purity Dehydroxy Vancomycin By Separation and Purification of Chromatography Again.

Further, according to another aspect of the present invention, the present invention also provides uses of dehydroxy vancomycin in preparing drugs for treatment of susceptible bacterial infections.

Moreover, the present invention provides a pharmaceutical composition further comprising a pharmaceutical effective amount of dehydroxy vancomycin, and pharmaceutical acceptable carriers or excipients. Wherein, said pharmaceutical composition also comprises vancomycin and/or vancomycin hydrochloride.

The present inventors separates and purifies samples of vancomycin hydrochloride to obtain high purity dehydroxy vancomycin which is used for science researches.

DESCRIPTION OF THE DRAWING

FIG. 1 is AU spectrogram of dehydroxy vancomycin of the present invention.

EXAMPLE 1

Separation and Purification of Vancomycin Hydrochloride Containing Dehydroxy Vancomycin Hydrochloride (1) Pre-Process of Fermentation Broth The fermentation broth is acidified and pH is adjusted to about 3.2 by dilute hydrochloric acid. In the process of acidification, sodium ferrocyanide (such as flocculating agent or filter aids) is added to the above fermentation broth in order to make the fermentation broth be filtered easily and obtain a fermentation filtrate having well quality.

(2) Adsorption, Desalting and Decolorization

D1300 resin is used as absorption resins. pH of the fermentation filtrate is adjusted to about 4.5 by 4N NaOH before the fermentation filtrate being absorbed by resin columns. The elution solution is a 80% acid aqueous solution of ethanol (pH=2.0). The elution solution is analysed by HPLC to obtain that the integral area ratio of vancomycin is usually about 75% and the average unit of vancomycin is over 10,000 m/ml.

The elution solution obtained by the above process is concentrated and desalted by nanofiltration, and then is decolorized by active carbons. Iron ion is removed by adding adequate sodium ferrocyanide and zinc sulfate. The above solution is collected and then desalted and concentrated by nanofiltration, then is decolorized by active carbon after adding 4N hydrochloric acid in order to adjust pH to about 2.8. And then the desalted and decolorized concentrated solution is obtained after adding sodium ferrocyanide and zinc sulfate to remove iron ion.

(3) Purification of Column Chromatography

The above concentrated solution passes Sephadex C-25 gel chromatography column, and gradient elutes by 0.1 M aqueous solution of $NH_4HCO_3$, collects elution solutions sectionally and merges purified solutions of chromatography. The purified solution of chromatography is desalted and concentrated by nanofiltration using 0.22 μm microporous filter membrane to obtain refined filtrate of chromatography. The refined filtrate is lyophilized to obtain aseptic material powders of vancomycin hydrochloride containing dehydroxy vancomycin hydrochloride after the refined filtrate is decolorized by active carbons and is filtered to remove hot source.

EXAMPLE 2

Preparing For High Purity Dehydroxy Vancomycin By Separation and Purification of Chromatography Again Material of Test:

Aseptic material powder of vancomycin hydrochloride containing dehydroxy vancomycin hydrochloride in the Example 1.

Apparatus of Test:

P6000 high pressure preparation pump;

UV6000 ultraviolet spectrophotometric detector with variable wavelength provided by Beijing Chuang Xin Tong Heng Technology Ltd.;

C18 MONOMERIC 5×25 cm preparation chromatography column (GRACE);

Rotary evaporator;

Rohm & Hass macroporous adsorption resin (XAD1600 resin) 250 ml grass chromatography column;

Some auxiliary grass apparatus.

Steps of Test:

1. Setting Separation Conditions of Chromatography

After optimizing, separation conditions of chromatography based on separation degree and efficiency are as follows:

Chromatography column: C18 MONOMERIC 5×25 cm preparation chromatography column (GRACE);

Detection wavelength: 280 nm;

Injection volume: 150 mg;

Flow rate: 60 ml/min;

Buffer: 4 ml triethylamine was dissolved in 1996 ml water, and then pH of the solution is adjusted to 3.2 by $H_3PO_4$ to obtain buffer;

Mobile phase is buffer:methanol=92:8

Carrier: XAD1600 resin

Please refer to FIG. 1 which is the AU spectrogram obtained, wherein, number 5 peak is the main peak of vancomycin hydrochloride, number 6 peak is our target impurity peak.

2. Collecting Fraction of Impurity and Removing Triethylamine Salt

Fifty parts of fraction are collected to obtain 6L collected solutions.

The collected solution is added into a chromatography column with 250 ml XAD1600 resin to be absorbed. After washing the column by a lot of water sufficiently, the column is eluted by 50% aqueous solution of methanol to collect 60 ml the eluted solution.

3. Concentration and Lyophilization 60 ml eluted solution is concentrated to about 5 ml by a rotary evaporator, and then is lyophilized at a lyophilizer room to obtain 35 mg target compound.

4. Identification of Structure

The proton signal peak in $^1HNMR$ spectrum of sample is generally similar to that of cancomycin, wherein three single peaks of methyl are δ0.85(3H, J=6.0 Hz), δ0.89(3H, J=6.5 Hz) and δ1.06(3H, J=6.5 Hz), and one single peak of methyl with δ2.26 is a signal to diagnose whether the structure of the sample has the same N-methylleucine(A) and vancosaminyl (Van) structure unit as vancomycin. There are three ortho-meta-coupled ABX system in aromatic areas: (1H, brs, $J_{meta}$<1.0 Hz,H-$E_4$), 6.71 (1H, d, $J_{ortho}$<8.0 Hz,H-$E_7$), 6.76 (1H, brd J=8 Hz, $J_{meta}$<1.0 Hz,H-$E_8$), 7.41(1H, brs, $J_{meta}$<1.0 Hz,H-$B_5$), 7.13(1H, d, $J_{ortho}$=8.0 Hz,H-$B_8$) 和 7.16 (1H, d, $J_{ortho}$<1.0 Hz,H-$B_9$), δ7.84 (1H, brs, $J_{meta}$<1.0 Hz,H-$F_5$), 7.31 (1H, d, $J_{ortho}$=8.0 Hz,H-$F_8$), and 7.45 (1H, brd J=8 Hz, $J_{meta}$<1.0 Hz,H-$F_9$), and there are two meta-coupled AB spin system in aromatic areas: δ5.47 (1H, brs, $J_{meta}$<1.0 Hz,H-$D_4$) and 5.20 (1H, brs, $J_{ortho}$<1.0 Hz,H-$D_8$) 6.38 (1H, brs, $J_{meta}$<1.0 Hz,H-$G_6$) and (1H, brs, $J_{meta}$<1.0 Hz,H-$G_8$).

Although the present invention has been described in connection with the above embodiments, it should be understood that the present invention is not limited to such preferred embodiments and procedures set forth above. The embodiments and procedures were chosen and described in order to best explain the principles of the invention and its practical application, to thereby enable others skilled in the art to best utilize the invention. It will be apparent to those skilled in the art that various substitution, modifications and changes may be thereto without departing from the scope and spirit of the invention. Therefore, the intention is intended to cover all alternative constructions and equivalents falling within the spirit and scope of the invention as defined only by the appended claims and equivalents thereto.

We claim:

1. A dehydroxy vancomycin having the general formula I as follows:

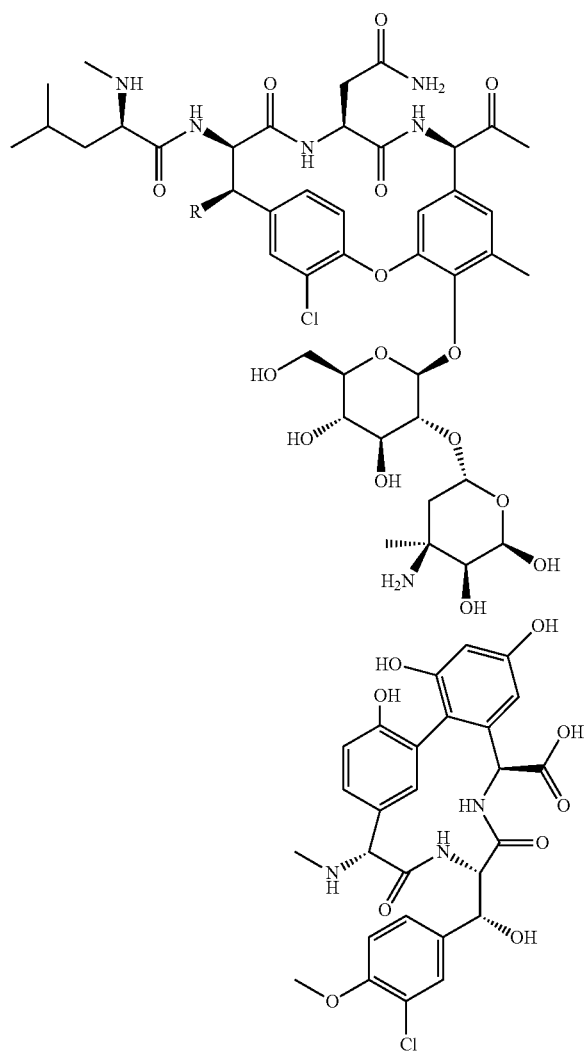

wherein, R represents H.

2. A method of preparing the dehydroxy vancomycin as claimed in claim 1, said method comprises the following steps:
   (1) preparing a concentrated vancomycin solution containing the dehydroxy vancomycin by fermentations of *Amycolatopsis Orientalis* with Deposit No. CGMC-CNO.1183;
   (2) separating and purifing the concentrated vancomycin solution to obtain a refined filtrate of vancomycin hydrochloride containing the dehydroxy vancomycin by column chromatography; and
   (3) further separating and purifing the refined filtrate to obtain the dehydroxy vancomycin by chromatography;
   wherein, in the step (2), separation and purification is processed by column chromatography in a gel chromatography column containing a salt-water mobile phase;
   in the step (3), separation and purification is processed by chromatography in a macroporous adsorption resin chromatography column containing a buffer-methanol mobile phase.

3. The method as claimed in claim 2, wherein pH of said concentrated vancomycin solution is adjusted to 2.8.

4. The method as claimed in claim 2, wherein said mobile phase is 0.1M aqueous solution of $NH_4HCO_3$ in the gel chromatography column.

5. The method as claimed in claim 2, wherein said gel includes dextran gel, polyacrylamide gel, agarose gel and polystyrene gel.

6. The method as claimed in claim 2, further comprising nanofiltrating, concentrating and desalting the column chromatography solution by using 0.22 μm microporous filter membrane in the separation and purification of column chromatography.

7. The method as claimed in claim 2, wherein said mobile phase includes buffer:methanol=92:8 in the separation and purification of chromatography.

8. The method as claimed in claim 2, wherein said buffer comprises triethylamine and phosphoric acid, and its pH=3.2.

9. The method as claimed in claim 2, wherein said macroporous adsorption resin is Rohm & Hass macroporous adsorption resin.

10. A pharmaceutical composition comprising a pharmaceutically effective amount of dehydroxy vancomycin according to claim 1, and a pharmaceutically acceptable carrier or excipient.

11. The pharmaceutical composition as claimed in claim 10, further comprising vancomycin and/or vancomycin hydrochloride.

12. A method for treating a bacterial infection, the method comprising the steps of:
    administering the composition according to claim 10 to an associated patient with the bacterial infection.

13. A method for treating a bacterial infection, the method comprising the steps of:
    administering the composition according to claim 11 to an associated patient with the bacterial infection.

* * * * *